United States Patent [19]

Milberger et al.

[11] 4,219,484

[45] Aug. 26, 1980

[54] PRODUCTION OF MALEIC ANHYDRIDE FROM FOUR-CARBON HYDROCARBONS USING CATALYSTS PREPARED BY WATER REFLUX TECHNIQUES

[75] Inventors: Ernest C. Milberger, Solon; Serge R. Dolhyj, Parma; Noel J. Bremer, Kent, all of Ohio

[73] Assignee: Standard Oil Company (Ohio), Ohio

[21] Appl. No.: 953,660

[22] Filed: Oct. 23, 1978

[51] Int. Cl.² ............................................. C07D 307/60
[52] U.S. Cl. .................................. 260/346.75; 252/437
[58] Field of Search ..................................... 260/346.75

[56] References Cited

U.S. PATENT DOCUMENTS

| | | | |
|---|---|---|---|
| 3,888,886 | 6/1975 | Young et al. | 260/346.75 |
| 3,907,835 | 9/1975 | Kobylinski et al. | 260/346.75 |
| 3,975,300 | 8/1976 | Burress | 252/435 |
| 3,977,998 | 8/1976 | Freerks et al. | 260/346.75 |
| 3,980,585 | 9/1976 | Kerr et al. | 252/437 |
| 3,985,775 | 10/1976 | Harrison | 260/346.75 |
| 4,002,650 | 1/1977 | Bremer et al. | 260/346.75 |
| 4,016,105 | 4/1977 | Kerr | 252/437 |
| 4,018,709 | 4/1977 | Barone et al. | 260/346.75 |
| 4,077,912 | 5/1978 | Dolhyj et al. | 252/461 |

Primary Examiner—Henry R. Jiles
Assistant Examiner—Bernard Dentz
Attorney, Agent, or Firm—Joseph G. Curatolo; Herbert D. Knudsen; Larry W. Evans

[57] ABSTRACT

Exceptionally reproducible catalysts comprising vanadium and phosphorus are obtained when the catalysts are prepared in an aqueous oxide slurry comprising vanadium, phosphorus and a mineral acid-free, inorganic reducing agent, which is capable of reducing the vanadium in the catalyst to a valence state below +5. Additional promoters may be selected from the group of elements of Group IB through VIB, VIII, lanthanides, actinides, and IA through VIA, excluding the elements H, N, O, C, Fr, Ra, and Po. Catalysts of particular interest consist of the elements vanadium, phosphorus, oxygen, and optionally at least one of Ta, Ce, Cr, Mn, Co, S, Cu, Sb, Fe, Bi, W, Mo, Hf, Zr, Th, an alkali metal and an alkaline earth metal.

27 Claims, No Drawings

1

PRODUCTION OF MALEIC ANHYDRIDE FROM FOUR-CARBON HYDROCARBONS USING CATALYSTS PREPARED BY WATER REFLUX TECHNIQUES

BACKGROUND OF THE INVENTION

1. Field of Invention

This invention relates to a method for preparing catalysts useful in the manufacture of dicarboxylic acid anhydride by the oxidation of hydrocarbons. More particularly, it is directed to the preparation of catalysts suitable for producing maleic anhydride from n-butane, n-butenes, 1,3-butadiene or a mixture thereof.

2. Description of the Prior Art

The preparation of oxide catalysts comprising vanadium and phosphorus for use in a vapor phase oxidation of a hydrocarbon feed is known in the art. Various catalysts have been proposed wherein during the catalytic preparatory step, pentavalent vanadium in the catalyst is reduced to a valence state below +5 using a reducing agent. The conventional methods of preparing the catalysts involve combining a vanadium compound, a phosphorus compound, and when specified, promoter element compounds in an acidic reducing medium under conditions which will provide vanadium in a valence state below +5 to form a catalyst precursor, thermally convertible to an oxide or an oxide complex catalyst; recovering the catalyst precursor; and calcining the catalyst precursor at a temperature of about 350° C. to about 600° C. for at least two hours. The reducing agents employed are usually solutions of mineral acids, particularly hydrochloric acid and phosphorous acid, or organic reducing agents, especially oxalic acid. For example, U.S. Pat. No. 3,985,775 to Harrison, et al. discloses the oxidation of n-butane using a mixed vanadium-phosphorus catalyst which is prepared by dissolving vanadium pentoxide in concentrated hydrochloric acid and adding 85% phosphoric acid to the resulting solution to yield a phosphorus to vanadium ratio of 0.5:1.0 (preferably 1.2:1.0). The resulting solution is then concentrated by heating to give a 50% solid aqueous slurry and then dried to constant weight at 150° C.; the dihydrate produced is preferably in or converted into particulate form for processing through the subsequent phase transition. U.S. Pat. No. 3,975,300 to Burress, et al. teaches the use of organic reducing agents, such as glycol, sucrose, ethylene glycol, and propylene glycol, in the preparation of vanadium-phosphorus complex catalysts. U.S. Pat. No. 4,002,650 to Bremer, et al. discloses the oxidation of n-butane using a catalyst of the formula $V_{0.5-3} P_{0.5-3} U_{0.1-0.5} O_x$. The preferred preparation of the catalyst involves refluxing a mixture of vanadium pentoxide, concentrated hydrochloric acid, and uranyl acetate. To this mixture is added 85% phosphoric acid. The mixture is evaporated at atmospheric pressure, dried at 110° C. and activated by heating in an air flow at 482° C. for 16 hours. U.S. Pat. No. 3,888,886 to Young, et al. discloses the oxidation of n-butane using a vanadium-phosphorus-oxygen complex catalyst having a phosphorus:vanadium atomic ratio of 0.5:2, promoted or modified with certain transition metals, preferably zirconium, chromium, iron or hafnium. These catalysts are prepared by refluxing a reaction mixture of vanadium oxide, phosphoric acid, a hydrogen halide (usually hydrochloric acid) and a specified promoter metal compound. U.S. Pat. No. 4,018,709 discloses the vapor phase oxidation of 4-carbon n-hydrocarbons using catalysts containing vanadium, phosphorus, uranium or tungsten or a mixture of elements from zinc, chromium, uranium, tungsten, cadmium, nickel, boron and silicon. Preferably, the catalytic complex also contains an alkali metal or an alkaline earth metal, especially lithium, sodium, magnesium or barium, as active components. Catalysts are prepared in a 37% hydrochloric acid solution. U.S. Pat. No. 3,980,585 to Kerr, et al. discloses the preparation of maleic anhydride from n-4C hydrocarbons in the presence of a catalyst containing vanadium, phosphorus, copper, oxygen, tellurium or a mixture of tellurium and hafnium or uranium. The process may also be conducted in the presence of a catalyst containing vanadium, phosphorus, copper, at least one of Te, Zr, Ni, Ce, W, Pd, Ag, Mn, Cr, Zn, Mo, Re, Sm, La, Hf, Ta, Th, Co, U, Sn and optionally an element from Groups IA or IIA. This patent exemplifies the use of oxalic acid in the preparation. U.S. Pat. No. 4,016,105 teaches the preparation of a V-P complex catalyst in an aqueous phosphoric acid solution using an organic acid or aldehyde and secondary alcohol as reducing agents.

U.S. Pat. No. 3,907,835 to Kobylinski discloses the production of maleic anhydride from benzene, butene, butadiene, butanol-2 or pentanol-2 using a catalyst of the formula $U_{1-3}O_{6-16}P_{1-4}H_{0-5}$, and optionally containing vanadium. Where vanadium is present, the catalyst is prepared by mixing an anhydrous uranium salt with vanadyl oxalate (vanadium to uranium is 0.1:1 to 0.1:2) and adding enough concentrated phosphoric acid to give a uranium to phosphorus ratio of 0.2:1 to 2:1 molar ratio and phosphorus to oxygen ratio of 0.1:1 to 0.35:1 to precipitate the catalyst which is dried at 29° C.–140° C. and heated to 425° C.–500° C. The vanadium content of this catalyst is preferably 6 to 40 weight percent. The anhydrous uranium salt is especially a phosphate prepared by the addition of a base to an aqueous solution to uranyl nitrate in concentrated phosphoric acid and drying and calcining to obtain catalytic precipitate.

Of particular interest is U.S. Pat. No. 3,977,998 to Freerks, et al., which discloses the oxidation of n-butane in the presence of a phosphorus-vanadium-oxygen complex catalyst, wherein the phosphorus to vanadium atom ratio is 1–2:2–1, the catalyst being prepared by (a) contacting a vanadium compound and a phosphorus compound in an acid solution containing a reducing agent under conditions which will provide at least 50 atom percent of vanadium in tetravalent form; (b) separating the prepared catalyst precursor; and (c) calcining the catalyst precursor at 350° C. to 660° C. for at least two hours, the improvement comprising that the calcination is effected in an inert atmosphere. The reducing agent may be a hydrogen halide acid or oxalic acid, but is preferably a mixture of phosphoric acid containing sufficient phosphorous acid to reduce $V^{+5}$. Preferred catalyst precursors have a phosphorus to vanadium atom ratio of 1:1 to 1.5:1, especially 1:1 to 1.2:1. Exemplified in this patent is the use of a catalyst of the formula $P_{1.05}V_1O_x$ prepared by digesting vanadium pentoxide in a mixture of water, 85% phosphoric acid and 99.4% phosphorous acid. This mixture was heated to 100° C. in an autoclave which was then sealed; the mixture was heated for 3 hours at 145° C. and a solid catalyst precursor was collected and slurried in 20 weight percent water. Viscous putty was extruded through a 0.35 cm. diameter die and cut into pellets, then air-dried and heated to 125° C. Pellets were heated in a muffle furnace to 350° C. for one hour and then to 375° C. an additional hour. The air in the furnace was replaced by nitrogen gas, and the temperature was raised to 500° C. over a five hour period. The catalyst was cooled rapidly to room temperature under nitrogen gas and possessed a 93 atom percent of vanadium as $V^{+4}$.

U.S. Pat. No. 4,077,912 to Dolhyj, et al. discloses that strongly exothermic reactions are controlled by the use of a catalyst which comprises (a) an inert support of at least about 20 microns in diameter, said support having an outer surface, and (b) a coating of a catalytically active material on the outside surface of the support which strongly adheres to the outer surface of the support. The Dolhyj, et al. patent broadly discloses that preferred catalysts contain the active catalytic component oxides of alkali metals, alkaline earth metals, vanadium, chromium, molybdenum, tungsten, manganese, iron, cobalt, nickel, copper, zinc, indium, thallium, tin, antimony, bismuth, phosphorus and arsenic. Especially preferred among these catalysts are those which contain at least the oxides of antimony and molybdenum. Specifically, the patent in claim 5 delineates the catalytically active oxide material and especially refers to the optional use of phosphorus as a catalytic constituent. By sharp contrast, the base catalyst employed in the present invention requires the presence of phosphorus as an integral catalytic constituent. Whereas phosphorus is a highly desirable active catalytic constituent of the catalysts employed in the present invention, the same is not shown as being effective as an ingredient in the catalysts containing vanadium which are utilized in the preparation of maleic anhydride at columns 4 and 5.

All of these teachings in the prior art have failed to achieve the desirable results obtained by the use of the present invention. The activity and quality of catalysts prepared using conventional prior art techniques are diverse because catalysts containing vanadium and phosphorus are especially sensitive to their mode of preparation. Using the present invention, reproducible catalysts of enhanced activity and selectivity are obtained.

SUMMARY OF THE INVENTION

It is an object of the present invention to provide an improved process for the vapor phase oxidation of n-butane, n-butenes, 1,3-butadiene or a mixture thereof to maleic anhydride.

It is a further object of this invention to provide a method for preparing a catalyst comprising oxides of vanadium and phosphorus.

In accordance with the present invention has been discovered a process for the preparation of maleic anhydride by the oxidation of n-butane, n-butenes, 1,3-butadiene, or a mixture thereof with molecular oxygen in the vapor phase at a reaction temperature of 250° C. to 600° C. in the presence of a uranium-free catalyst comprising the mixed oxides of vanadium and phosphorus, the improvement herein the catalyst is prepared by:

(a) forming an aqueous oxide slurry of a vanadium compound containing pentavalent vanadium;

(b) adding to said aqueous oxide slurry a mineral acid-free, inorganic reducing agent capable of reducing said pentavalent vanadium to a valence state below +5 to obtain an aqueous slurry containing reduced vanadium, wherein said reducing agent is selected from the group consisting of ammonia, hydrazine, hydrazine hydrate, a finely divided metal or colloidal metal;

(c) adding a phosphorus compound containing pentavalent phosphorus before the addition of the reducing agent or after the addition of the reducing agent;

(d) removing the water from the resulting slurry to form a dried catalyst and (e) calcining the dried catalyst at a temperature of 200° C. to 600° C.

Effective results are observed when the catalyst is based solely upon vanadium, phosphorus and oxygen, but it is preferred that additional promoters be selected from the group consisting of elements of Group IB thru VIB, VIII, lanthanides, actinides, and Group IA thru VIA, excluding the elements H, N, O, C, Fr, Ra, and Po. Catalysts of particular interest consist of the elements vanadium, phosphorus, oxygen and optionally at least one of tantalum, cerium, chromium, manganese, cobalt, copper, antimony, iron, bismuth, tungsten, hafnium, zirconium, thorium, an alkaline earth metal, sulfur and an alkali metal.

Although preferably the compound containing pentavalent vanadium is pre-reduced before reaction with the compound containing pentavalent phosphorus, beneficial results are achieved by reacting the compound containing pentavalent vanadium with the compound containing pentavalent phosphorus followed by reaction with a reducing agent, or by reacting the three components together followed by the addition of compounds containing the respective promoter elements. However, superior results are observed when the compounds containing the respective promoter elements are added to the aqueous slurry containing reduced vanadium immediately preceeding the addition of the compound containing pentavalent phosphorus.

Excellent results may be obtained using catalysts wherein the phosphorus to vanadium atom ratio is 0.1:15 to 15:0.1. Especially desirable results are observed using catalysts wherein the phosphorus to vanadium atom ratio is 0.5:3 to 3:0.5; and catalysts wherein a finely divided metal or colloidal metal is present in the catalyst in an atomic range of 0.01:5.

A catalyst prepared in accordance with the present invention whereby favorable results are achieved is described by the formula $$V_a P_b X_c O_x$$

wherein a and b are 0.1 to 15;

c is 0 to 5;

x is a positive number of oxygens required to satisfy the valence requirements of the other elements present; and wherein X is at least one element selected from the group consisting of tantalum, cerium, chromium, manganese, cobalt, copper, antimony, iron, bismuth, tungsten, molybdenum, sulfur and uranium.

Especially desirable results are obtained using catalysts wherein a and b are 0.5 to 15; catalysts wherein a and b are 0.5 to 3; and catalysts wherein a finely divided metal or colloidal metal is present in the catalyst in an atomic range of 0.01 to 5.

The method employed in preparing the catalyst is critical to the process for producing maleic anhydride. Maximum conversions of maleic anhydride are obtained where the starting material is n-butane or n-butenes. Essentially all the product produced in this process is maleic anhydride with only minor amounts of lower acids being detected.

The method employed in preparing the catalyst departs from the classical procedures involving reducing the vanadium in the catalyst to a valence state below +5 using an acid, such as a hydrogen halide acid or an organic acid, in particular hydrochloric acid or oxalic acid, as the reducing agent. By the preferred procedure of the invention a compound containing pentavalent vanadium in an aqueous suspension is pre-reduced in a controlled manner so that at least some of the vanadium is reduced to a valence state below +5 before the compound containing pentavalent vanadium is mixed with a compound containing pentavalent phosphorus, followed by drying the aqueous mixture and calcining the resulting product.

The method employed preferably involves the simple mixing of the pentavalent vanadium compound and the reducing agent. The mixing of the components may be carried out mechanically in a blender or in a ball mill, or the respective oxides may be mixed as a slurry in water. Generally, the phosphorus compound is added at this juncture. This initial step is followed by calcination at a moderate temperature, generally not above 600° C. It is hypothesized that the color which develops in the catalyst is the result of the reduction of vanadium, at least in part, to a lower oxidation state in the oxidation-reduction reaction occur-ring between pentavalent vanadium and the reducing agent.

Suitable vanadium compounds containing pentavalent vanadium include: vanadium pentoxide or vanadium salts, such as ammonium metavanadate, and vanadium oxytrihalides, however, vanadium pentoxide, is preferred. Suitable phosphorus compounds containing pentavalent phosphorus include: phosphoric acid, phosphorus pentoxide, or phosphorus perhalides, such as phosphorus pentachloride, however, phosphoric acid and phosphorus pentoxide are preferred.

Representative examples of suitable reducing agents include hydrazine, hydrazine hydrate, ammonia, or finely divided or colloidal metals of molydenum, tungsten, magnesium, aluminum, or nickel. When powdered metals are employed, the amount of metal reacted ranges from 0.01 to 5 gram-atoms per mole of the pentavalent vanadium present. It is to be understood that in accordance with the present invention suitable reducing agents do not include inorganic acids, such as phosphorous acid and hydrogen halide acids, or organic reducing agents, such as oxalic acid, citric acid, formic acid, ascorbic acid, malic acid, glycol, sucrose, ethylene glycol, and propylene glycol, aldehydes, such as formaldehyde and acetaldehyde, or alcohols.

An especially preferred procedure of the invention involves refluxing an aqueous slurry of a vanadium compound containing pentavalent vanadium, a reducing agent, and at least one compound containing the respective promoter elements for a period of ½ hour to 16 hours and preferably from about 1 to 4 hours. Following this the pentavalent phosphorus compound is added and the slurry is heated from ½ to 16 hours, and preferably from about 1 to 4 hours. The amount of water present in the solution can range from 500 to 2000 mls. per gram-atom of vanadium present. During the initial heating period the slurry darkens in color. Water is removed from the slurry by evaporation until a thick homogenous material is obtained which on drying at 110° C. overnight emerges as a solid.

A reproducible method of combining the catalytic ingredients comprises:

(a) refluxing an aqueous oxide slurry containing vanadium pentoxide;

(b) adding to said aqueous slurry a mineral acidfree, inorganic reducing agent capable of reducing the vanadium in the vanadium pentoxide to a valence state below +5 to obtain an aqueous slurry containing reduced vanadium, wherein said reducing agent is selected from the group consisting of ammonia, hydrazine, hydrazine hydrate, a finely divided metal or colloidal metal;

(c) adding phosphoric acid before the addition of the reducing agent or after the addition of the reducing agent;

(d) removing the water from the resulting slurry to form a dried catalyst; and (e) calcining said dried catalyst at a temperature of 200° C. to 600° C.

Excellent results are obtained using a coated catalyst consisting essentially of an inert support material having a diameter of at least 20 microns and an outer surface, and a continuous coating of said active catalyst on said inert support strongly adhering to the outer surface of said support. The special coated catalyst consists of an inert support material having an outer surface and a coating of the active catalytic material on this outer surface.

The support material for the catalyst forms the inner core of the catalyst. This is an essentially inert support and may have substantially any particle size although a diameter of at least 20 microns is preferred. Especially preferred in the present invention for use in a commercial reactor are those supports which are spherical and which have a diameter of about 0.2 cms. to about 2 cms. Suitable examples of essentially inert support materials include: Alundum[R], silica, alumina, alumina-silica, silicon carbide, titania, and zirconia. Especially preferred among these supports are Alundum[R], silica, alumina and alumina-silica.

The catalysts may contain essentially any proportion of support and catalytically active material. The limits of this relationship are only set by the relative ability of the catalyst and support material to accommodate each other. Preferred catalysts contain about 10% to about 100% by weight of catalytically active material based on the weight of the support.

The preparation of these coated catalysts can be accomplished by various techniques. The basic method of preparing these catalysts is to partially wet the support material with a liquid. The support cannot be wet on the outer surface of the total mass. It should be dry to the touch. If the support is wet, then the active catalytic material will agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum and adding the active catalytic material until none is taken up by the support. This is very economically done.

The catalyst is activated by calcining it at a temperature of 200° C. to 600° C. for a period of up to 5 hours or more. A preferred activation of the catalyst is accomplished by passing a mixture of steam and air or air alone over the catalyst at a temperature of 250° C. to 500° C. for a period of about 1 to 5 hours. The hydrocarbon reactant may be n-butane, n-butenes, 1,3-butadiene or a mixture thereof. Preferred is the use of n-butane, n-butenes or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, Alundum$^{(R)}$, silicon carbide, boron phosphate, zirconia, titania, and the like. The catalysts are conveniently used in a fixed-bed reactor using tablets, pellets or the like, or in a fluid-bed reactor using a catalyst preferably having a particle size of less than about 300 microns. The contact time may be as low as a fraction of a second or as high as 50 seconds. The reaction may be conducted at atmospheric, superatmospheric or subatmospheric pressure.

SPECIFIC EMBODIMENTS

Examples 1 to 19 and Comparative Examples 1 to 4

Various catalysts of the invention were prepared as follows:

EXAMPLE 1

$V_{1.0}P_{1.15}O_x + W°_{0.166}$ 36.37 grams of $V_2O_5$ and 12.26 grams of powdered tungsten metal were refluxed on a hot plate for $2\frac{1}{4}$ hours. 53.0 grams of 85% $H_3PO_4$ were added and the mixture was refluxed for an additional $1\frac{1}{2}$ hours, evaporated overnight over a steam bath, and dried for two days in an oven at 115° C. The resulting sample was divided into two portions. The first portion had some black glassy material on its outer surface, most of which was manually removed. This first portion, bluish-brown in appearance, was calcined at 482° C. for two hours.

The second portion, deep greenish-brown in appearance, did not have black glassy material on its surface; said second portion was calcined at 482° C. for 2 hours resulting in a catalyst which was deep green in appearance.

EXAMPLE 2

10.7% $(Sb_2B_3V_{12}O_x + W°_{1.32}) + 89.3\%$ Norton SA203 Alundum 181.9 grams of $V_2O_5$ were slurried in about 1 liter distilled water in a 2 liter beaker equipped with a magnetic bar stirrer topped with a round bottomed reflux flask. To this solution were added 40.44 grams of tungsten metal powder. The resulting slurry was heated to boiling and allowed to reflux for several hours; the slurry was deep blue-black in appearance. The slurry was allowed to stand overnight with constant stirring. The total weight of the slurry was 1313 grams, which contained 181.9 grams of $V_2O_5$. 342 grams of this slurry was employed; 15 grams of $H_3PO_4$ were added thereto and the resulting slurry was refluxed for about 1 hour followed by the addition of 12.66 grams of $Sb_2O_3$. The final slurry was refluxed an additional 2 hours, evaporated to a thick paste, dried overnight at 110° C., and ground and screened to 50 mesh size. A portion of this powder was coated onto 10/30 mesh Norton SA203 Alundum$^{(R)}$ by taking 25 grams Alundum$^{(R)}$, partially wetting the Alundum$^{(R)}$ with 2 grams of water, and adding 12.5 grams of active catalytic material prepared above in five equal portions. During and after each addition, the Alundum$^{(R)}$ was rolled in a glass jar. The final product was dried overnight at about 110° C. A hard uniform material was obtained that consisted of an inner core of the Alundum$^{(R)}$ support with the continuous, strongly adhering coat of the powder on the outside surface of the support.

EXAMPLE 3

$V_{1.0}P_{1.20}Cr_{0.20}O_x$ 30 grams of $V_2O_5$ were slurried in about 600 mls. of distilled water, followed by the addition of 4.1 grams of 99% to 100% hydrazine hydrate. The resulting mixture was refluxed for one hour and cooled overnight. The next day 45.9 grams of 85% $H_3PO_4$ were added followed by the immediate addition of 8.31 grams of $(NH_4)_2Cr_2O_7$. The resulting mixture was placed on a hotplate and refluxed for 1 hour 45 minutes, boiled to dryness, dried at 110° C. overnight, and calcined at 482° C. for 2 hours.

EXAMPLE 4

$V_{1.2}P_{1.2}Cu_{0.20}O_x$

This catalyst was prepared in the same manner described in Example 3, except the $(NH_4)_2Cr_2O_7$ was replaced with 14.986 grams of copper acetate taken as 35% CuO in Cu(acet)$_2$.

EXAMPLE 5

$V_{1.0}P_{1.19}Zn_{0.19}O_x$ 100 grams of $V_2O_5$ were slurried in water and brought to a boil; the slurry was brown in appearance. 1.45 grams of $N_2H_4$ were added in the form of a hydrate, the slurry turned dark green and was refluxed for 2 hours. 36.43 grams of 85% $H_3PO_4$ and 11.467 grams of Zn acetate were added and refluxed for two hours. The slurry remained green in appearance. $H_2O$ was boiled-off over a 4 hour period and dried at 110° C. overnight. The resulting material was dark green in appearance and quite hard.

COMPARATIVE EXAMPLE 1

$V_{1.0}P_{1.15}O_x$ 33.6 grams of vanadium pentoxide were digested in 437.5 mls. of hydrochloric acid and refluxed for 3 to 4 hours. To this mixture were added 48.65 grams of 85% phosphoric acid and refluxing was continued an additional 6 hours. The resulting mixture was evaporated to dryness, and dried overnight at 110° C. The product consisted of two distinct crystalline phases: one was blue and another was gold in appearance. Calcination was conducted for 1 hour at 360° C. in air.

COMPARATIVE EXAMPLE 2

A catalyst of the formula $V_{1.0}P_{1.0}O_5$ was prepared by preforming a $V_2O_5$-$P_2O_5$ complex as follows: 50 grams of vanadium pentoxide were ball milled with 39 grams of phosphorus pentoxide and heated at 850° C. in an oven overnight. The next day, the temperature was incrementally decreased at a rate of 40° C. per hour until a temperature of 650° C. was reached. Heating was terminated, and the mixture was cooled. The product had the appearance of being hard, glassy and green-black in color, covered with small green-yellow crystals.

EXAMPLES 6 TO 19 AND COMPARATIVE EXAMPLES 3 AND 4

Preparation of maleic anhydride using various catalysts of the invention compared with use of prior art catalysts.

The catalysts were prepared in the same manner as shown above using the appropriate ratios of ingredients.

A 20 cc fixed-bed reactor was constructed equipped with a split-feed induction system. Catalysts prepared as described below were charged to the reactor and heated to the reaction temperature and n-butane or 2-butene was reacted with air in the proportions specified in Tables I to IV at an apparent contact time of 1 to 2 seconds. N-butane or 2-butene was premixed with a small portion of the total quantity of air in a 30 cm. packed tube as the mixture was regulated to a splitter allowing only a split stream to flow to the reactor. The remainder of the air was added just prior to the inlet of the reactor. Liquid product was recovered in aqueous scrubbers and titrated for total acid. When n-butane was reacted, product samples were found to be at least 98% maleic anhydride; and when 2-butene was reacted, product samples were found to be 80% to 90% maleic anhydride. Off-gas analyses for 4-carbon hydrocarbons, carbon monoxide, carbon dioxide, and oxygen were determined using a Carle A.G.C. 111 equipped with a heated column oven, wherein the column consisted of molecular sieves and sebacyl chloride on chromosorb. The reaction conditions and results of the experiments are shown in Tables I to IV. The following definitions are used in measuring the carbon atoms in the feed and the products.

$$\% \text{ Single Pass Yield to Total Acid} = \frac{\text{moles carbon as total acid}}{\text{moles carbon as hydrocarbon fed}} \times 100$$

$$\% \text{ Selectivity to Total Acid} = \frac{\text{moles carbon as total acid}}{\text{moles carbon fed as hydrocarbon} - \text{moles carbon as hydrocarbon recovered}} \times 100$$

TABLE I

Oxidation of n-Butane Using a Catalyst of the Invention Compared with Use of Prior Art Catalysts

| | | Temp. °C. | | Results, % Single Pass Yield | Selectivity, | Hours On | Air/n-Butane | Contact Time |
|---|---|---|---|---|---|---|---|---|
| Ex. | Catalyst | Bath | Reactor | Total Acid* | Total Acid | Stream | Ratio | Seconds |
| 6 | $V_{1.0}P_{1.15}O_x + W°_{0.166}$ (Duplicate) | 518.33 | 529.44 | 34.10 | 39.0 | 20.0 | 90.0 | 1.28 |
| 7 | $V_{1.0}P_{1.15}O_x + W°_{0.166}$ (Duplicate) | 496.11 | 511.67 | 39.70 | 42.0 | 25.4 | 92.0 | 1.32 |
| 8 | $V_{1.0}P_{1.15}O_x + W°_{0.166}$ (Duplicate) | 527.78 | 540.00 | 34.70 | 37.0 | 23.8 | 90.0 | 1.26 |
| 9 | $V_{1.0}P_{1.15}O_x + W°_{0.166}$ (Duplicate) | 485.00 | 496.11 | 38.70 | 43.0 | 1.2 | 91.0 | 1.30 |
| 10 | $V_{1.0}P_{1.15}O_x + W°_{0.166}$ | 510.00 | 525.56 | 34.10 | 36.0 | 5.4 | 92.0 | 1.29 |
| C-3 | $V_{1.0}P_{1.15}O_x$ (HCl digestion) | 499.00 | 505.00 | 30.43 | 54.5 | 6.4 | 112.0 | |
| C-4 | $V_{1.0}P_{1.0}O_5$ ($P_2O_5$ + $V_2O_5$) | 537.80 | 537.80 | 1.22 | 13.4 | 46.0 | 89.0 | |

*at least 98% pure maleic anhydride.

TABLE II

Oxidation of 2-Butene Using Various Catalysts of the Invention

| | | Temp. °C. | | Results, % Single Pass Yield | Selectivity, | Hours On | Air/n-Butene | Contact Time |
|---|---|---|---|---|---|---|---|---|
| Ex. | Catalyst | Bath | Reactor | Total Acid* | Total Acid | Stream | Ratio | Seconds |
| 11 | $V_{1.0}P_{1.15}O_x + W°_{0.166}$ (Duplicate) | 372.78 | 382.22 | 46.90 | 49.1 | 23.3 | 87.0 | 1.60 |
| 12 | $V_{1.0}P_{1.15}O_x + W°_{0.166}$ | 397.22 | 418.33 | 43.70 | 46.1 | 18.2 | 89.0 | 1.48 |
| 13 | 10.7% ($Sb_2P_3V_{12}O_x + W°_{1.32}$) + 89.3% Norton SA203 Alundum | 454.44 | 464.44 | 25.06 | 27.0 | 19.0 | 52.9 | 1.19 |

*Measured as total acid, of which 80% to 90% was maleic anhydride.

TABLE III

Oxidation of n-Butane Using Catalysts of the Invention

| Ex. | Catalyst | Temp. °C. Bath | Temp. °C. Reactor | Total Acid* | Results, % Single Pass Yield Selectivity, Total Acid | Hours On Stream | Air/n-Butane Ratio | Contact Time Seconds |
|---|---|---|---|---|---|---|---|---|
| 15 | $VP_{1.2}Cr_{0.2}O_x$ | 507.00 | 523.00 | 13.80 | 18.3 | 47.4 | 65.5 | 1.15 |
| 16 | $VP_{1.2}Cu_{0.2}O_x$ | 509.00 | 525.00 | 23.80 | 25.7 | 50.8 | 66.9 | 1.15 |
| 17 | $VP_{1.19}Zn_{0.19}O_x$ | 456.00 | 462.00 | 18.10 | 22.0 | 0.5 | 93.0 | 1.80 |

*at least 98% pure maleic anhydride.

TABLE IV

Oxidation of 2-Butene Using Catalysts of the Invention

| Ex. | Catalyst | Temp. °C. Bath | Temp. °C. Reactor | Total Acid* | Results, % Single Pass Yield Selectivity, Total Acid | Hours On Stream | Air/n-Butene Ratio | Contact Time Seconds |
|---|---|---|---|---|---|---|---|---|
| 18 | $VP_{1.2}Cr_{0.2}O_x$ | 362.00 | 388.00 | 38.50 | 38.5 | 23.6 | 77.5 | 1.40 |
| 19 | $VP_{1.2}Cu_{0.2}O_x$ | 382.00 | 403.00 | 47.30 | 47.3 | 26.5 | 77.1 | 1.35 |

*measured as total acid, of which 80% to 90% was maleic anhydride.

We claim:

1. In a process for the production of maleic anhydride by the oxidation of n-butane, n-butenes, 1,3-butadiene or a mixture thereof with molecular oxygen in the vapor phase at a reaction temperature of 250° C. to 600° C. in the presence of a catalyst comprising the mixed oxides of vanadium and phosphorus, the improvement wherein the catalyst is prepared by
   (a) forming an aqueous oxide slurry of a vanadium compound containing pentavalent vanadium;
   (b) adding to said aqueous oxide slurry a mineral acid-free, inorganic reducing agent capable of reducing said pentavalent vanadium to a valence state below +5 to obtain an aqueous slurry containing reduced vanadium, wherein said reducing agent is selected from the group consisting of ammonia, hydrazine, hydrazine hydrate, a finely divided metal or colloidal metal;
   (c) adding a phosphorus compound containing pentavalent phosphorus before the addition of the reducing agent or after the addition of the reducing agent;
   (d) heating said aqueous oxide slurry under reflux conditions;
   (e) removing the water from the resulting slurry to form a dried catalyst; and
   (f) calcining the dried catalyst at a temperature of 250° C. to 600° C.

2. The process of claim 1 wherein n-butane is reacted.

3. The process of claim 1 wherein an n-butene is reacted.

4. The process of claim 1 wherein the phosphorus to vanadium atom ratio is 0.1:15 to 15:0.1.

5. The process of claim 1 wherein the finely divided metal or colloidal metal is present in the catalyst in an atomic range of 0.01 to 5.

6. The process of claim 1 wherein the reducing agent is selected from the group consisting of hydrazine, hydrazine hydrate and a finely divided metal or colloidal metal.

7. The process of claim 6 wherein the finely divided metal is tungsten.

8. The process of claim 1 wherein the phosphorus to vanadium atom ratio is 0.5:3 to 3:0.5.

9. The process of claim 1 wherein the compound containing pentavalent vanadium is vanadium pentoxide.

10. The process of claim 1 wherein the compound containing pentavalent phosphorus is phosphoric acid.

11. The process of claim 1 wherein the catalyst is prepared in the absence of a hydrogen halide, or an organic reducing agent.

12. The process of claim 11 wherein the organic reducing agent is an organic acid, aldehyde or secondary alcohol.

13. The process of claim 1 wherein the compound containing pentavalent phosphorus is added after the addition of the reducing agent.

14. In a process for producing maleic anhydride from n-butane, n-butenes, 1,3-butadiene or a mixture thereof with molecular oxygen in the vapor phase at a reaction temperature of 250° C. to 600° C. in the presence of a catalyst comprising the mixed oxides of vanadium and phosphorus, the improvement wherein the catalyst is prepared by
   (a) forming an aqueous oxide slurry of vanadium pentoxide;
   (b) adding to said aqueous oxide slurry a mineral acid-free, inorganic reducing agent capable of reducing the vanadium in the vanadium pentoxide to a valence state below +5 to obtain an aqueous slurry containing reduced vanadium, wherein said reducing agent is selected from the group consisting of ammonia, hydrazine, hydrazine hydrate, a finely divided metal or colloidal metal;
   (c) adding phosphoric acid before the addition of the reducing agent or after the addition of the reducing agent;
   (d) heating said aqueous oxide slurry under reflux conditions;
   (e) removing the water from the resulting slurry to form a dried catalyst; and
   (f) calcining said dried catalyst at a temperature of 250° C. to 600° C.

15. The process of claim 14 wherein the reducing agent is a finely divided metal or colloidal metal, hydrazine or hydrazine hydrate.

16. The process of claim 14 wherein the finely divided metal or colloidal metal is tungsten.

17. The process of claim 14 wherein phosphoric acid is added after the addition of the reducing agent.

18. The process of claim 1 wherein compounds containing respective optional promoter elements of tantalum, cerium, chromium, manganese, cobalt, copper, antimony, iron, bismuth, tungsten, molybdenum, alkaline earth metal, an alkali metal, hafnium, zirconium, thorium and sulfur may be added during the preparation of the catalyst immediately after step (a), immediately after step (b), or after step (c).

19. The process of claim 18 wherein the catalyst is described by the formula $$V_a P_b X_c O_x$$

wherein a and b are 0.1 to 15;
 c is 0 to 5;
 x is a positive number of oxygens required to satisfy the valence requirements of the other elements present; and
wherein X is at least one element selected from the group consisting of tantalum, cerium, chromium, manganese, cobalt, copper, antimony, iron, bismuth, tungsten, molybdenum, sulfur, alkaline earth metal, an alkali metal, hafnium, zirconium and thorium.

20. The process of claim 19 wherein c is present in the catalyst in an atomic range of 0.01 to 5.

21. The process of claim 19 wherein a and b are from 0.5 to 15.

22. The process of claim 19 wherein a and b are from 0.5 to 3.

23. The process of claim 1 wherein the active catalytic material is coated on an inert support.

24. The process of claim 23 wherein the catalyst consists essentially of an inert support material having a diameter of at least 20 microns and an outer surface and a continuous coating of said active catalytic material strongly adhering to the outer surface of said support.

25. The process of claim 24 wherein the active catalytic material is about 10% to about 100% by weight of the inert support.

26. The process of claim 24 wherein the support is selected from the group consisting of silica, alumina, alumina-silica, silicon carbide, titania and zirconia.

27. The process of claim 24 wherein the particle size of the inert support is 0.2 cms. to 2 cms.

* * * * *